United States Patent [19]

Seto et al.

[11] Patent Number: 4,514,490

[45] Date of Patent: Apr. 30, 1985

[54] COLOR PHOTOGRAPHIC LIGHT-SENSITIVE MATERIAL

[75] Inventors: Nobuo Seto; Takayoshi Kamio; Kozo Aoki, all of Kanagawa, Japan

[73] Assignee: Fuji Photo Film Co., Ltd., Japan

[21] Appl. No.: 530,437

[22] Filed: Sep. 8, 1983

[30] Foreign Application Priority Data

Sep. 8, 1982 [JP] Japan ................. 57-156404

[51] Int. Cl.$^3$ ................. G03C 1/46
[52] U.S. Cl. ................. 430/505; 430/551; 430/554; 430/555; 430/558
[58] Field of Search ............. 430/372, 505, 551, 558, 430/554, 555

[56] References Cited

U.S. PATENT DOCUMENTS 3,519,429 7/1970 Lestina ................. 430/558
4,332,886 6/1982 Aoki et al. ................. 430/551
4,383,027 5/1983 Ishikawa et al. ................. 430/555

Primary Examiner—J. Travis Brown

Attorney, Agent, or Firm—Sughrue, Mion, Zinn, Macpeak and Seas

[57] ABSTRACT

A color photographic light-sensitive material comprising a support having thereon a silver halide emulsion layer containing therein a coupler represented by the following general formula (I):

$$Q\text{-}B \qquad \qquad (I)$$

wherein Q represents a coupler residue capable of forming a magenta color image upon the coupling reaction with an oxidation product of a developing agent; and B represents a group containing an unsubstituted or substituted methylenedioxybenzene group.

The magenta coupler containing a methylenedioxybenzene group is useful in preventing the formation of yellow stain due to light irradiation in unexposed areas of a color photographic light-sensitive material after color development processing. Color images formed from the coupler are resistant to fading even if the color images obtained after color development processing are irradiated with light.

13 Claims, No Drawings

COLOR PHOTOGRAPHIC LIGHT-SENSITIVE MATERIAL

FIELD OF THE INVENTION

The present invention relates to a color photographic light-sensitive material. More particularly, it relates to a color photographic light-sensitive material containing a novel coupler having a methylenedioxybenzene group or a derivative thereof for the purpose of improving light fastness of the coupler and a dye formed upon the coupling reaction of the coupler with an oxidation product of a developing agent.

BACKGROUND OF THE INVENTION

After exposing a silver halide photographic light-sensitive material to light, the material is subjected to color development, an oxidized developing agent reacts with a coupler to form a dye, with a dye image thus being formed. In this system, a subtractive process is generally used for color reproduction, in which blue, green and red colors are reproduced by forming yellow, magenta and cyan color images which are in complementary relation thereto, respectively. In general, acrylacetamide or dibenzoylmethane type couplers are employed for forming yellow color images; pyrazolone, cyanoacetyl coumarone or indazolone type couplers are used for forming magenta color images; and phenol type couplers, for example, phenols and naphthols, are utilized for forming cyan color images.

To produce color photographs, couplers which form dyes are incorporated in a developer or in a light-sensitive photographic emulsion layer(s).

It has been strongly desired to preserve color images as they were after development for a long period of time in the field of color photographic light-sensitive materials. The most fundamental method in order to resolve this problem is to improve fastness of the coupler and the dye which is formed from the coupler and the oxidation product of the developing agent.

Various couplers for forming magenta color images are known. For example, the couplers described in U.S. Pat. No. 3,935,015 are 3-(acylaminoanilino)-5-pyrazolones represented by the general formula (M) described below and are well known:

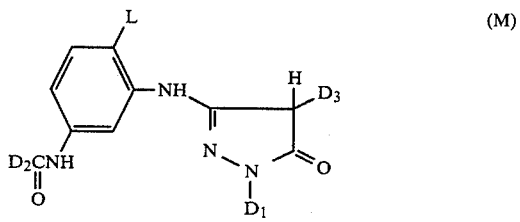

(M)

wherein $D_1$ represents an aryl group or a heterocyclic group, $D_2$ represents a straight chain, branched chain or cyclic alkyl group having from 7 to 23 carbon atoms, $D_3$ represents a coupling-off group, and L represents a halogen atom or an alkoxy group having from 1 to 18 carbon atoms.

These couplers have the characteristics that the undesired absorption of magenta azomethine dyes obtained upon color formation using the same in the red light region is low, the cut-off of the main absorption is good at the longer wavelength side, and magenta color images having a high color density are obtained because the coupling speed is high. Furthermore, the solubility in organic solvents having a high boiling point is improved, so that, after dissolving these couplers in organic solvents, the couplers can be emulsion-dispersed in an aqueous medium in the form of fine colloidal particles and then added to emulsions.

However, these couplers have the disadvantages that the degree of yellow staining at the unexposed portion after color development processing is high, and this degree of yellow staining increases upon light irradiation. They have the further disadvantages that color fading of the magenta color images obtained upon color development using these compounds occurs to a significant degree upon irradiation with light, and the color balance required for color photography is damaged by exposure to light. These disadvantages become fatal defects for color photographic light-sensitive materials, such as color printing papers and the like. Thus, improved couplers which do not have these disadvantages have been strongly desired.

SUMMARY OF THE INVENTION

An object of the present invention is to provide a coupler with which the formation of yellow stain at the unexposed areas of a color photographic light-sensitive material after color development processing is minimized, i.e., with which yellow stain does not occur initially nor does a yellow stain occur later upon irradiation of the dye image with light.

Another object of the present invention is to provide a coupler having the property that color images formed therefrom are resistant to fading even if the magenta color images obtained after color development are irradiated with light.

These and other objects of the present invention will become more apparent from the detailed description of the invention and the examples given hereinbelow.

These objects of the present invention are achieved by a color photographic light-sensitive material comprising a support having thereon a silver halide emulsion layer containing therein a coupler represented by the following general formula (I):

Q-B    (I)

wherein Q represents a coupler residue capable of forming a magenta color image upon the coupling reaction with an oxidation product of a developing agent; and B represents a group containing an unsubstituted or substituted methylenedioxybenzene group.

DETAILED DESCRIPTION OF THE INVENTION

Couplers which are useful for the present invention include compounds represented by the following general formula (I):

Q-B    (I)

wherein Q represents a coupler residue capable of forming a magenta color image upon the coupling reaction with the oxidation product of a developing agent (for example, a 3-anilino-5-pyrazolone type magenta color forming coupler residue, a 3-benzoylamino-5-pyrazolone type magenta color forming coupler residue, a pyrazolo[1,5-a]benzimidazole type magenta color forming coupler residue, a 1H-pyrazolo[3,2-c]-S-triazole type magenta color forming coupler residue, etc.); and B represents a group containing an unsubstituted or substituted methylenedioxybenzene group.

Of these couplers used in the present invention, more preferred couplers are those represented by the following general formula (II):

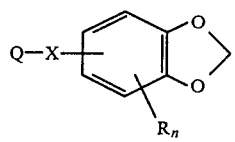

wherein Q has the same meaning as defined above; R represents a straight chain, branched chain or cyclic alkyl group preferably having from 1 to 22 carbon atoms, more preferably from 1 to 12 carbon atoms (for example, a methyl group, a tert-butyl group, a cyclohexyl group, a dodecyl group, etc.), an alkenyl group preferably having from 2 to 22 carbon atoms, more preferably from 2 to 12 carbon atoms (for example, an allyl group, etc.), an aralkyl group preferably having from 7 to 22 carbon atoms, more preferably from 7 to 12 carbon atoms (for example, a benzyl group, a phenethyl group, etc.), a halogen atom (for example, a fluorine atom, a chlorine atom, etc.), an alkoxy group preferably having from 1 to 22 carbon atoms, more preferably from 1 to 12 carbon atoms (for example, a methoxy group, an octyloxy group, etc.) or a hydroxy group. The alkyl moiety and the aryl moiety in these groups can be substituted with one or more substituents selected from a halogen atom, a nitro group, a cyano group, an aryl group (for example, a phenyl group, a naphthyl group, etc.), an alkoxy group (for example, a methoxy group, an ethoxy group, etc.), an aryloxy group (for example, a phenyloxy group, a naphthyloxy group, etc.), a carboxy group, an alkylcarbonyl group (for example, an acetyl group, a tetradecanoyl group, etc.), an arylcarbonyl group (for example, a benzoyl group, etc.), an alkoxycarbonyl group (for example, a methoxycarbonyl group, a benzyloxycarbonyl group, etc.), an aryloxycarbonyl group (for example, a phenyloxycarbonyl group, a p-tolyloxycarbonyl group, etc.), an acyloxy group (for example, an acetyloxy group, a tetradecanoyloxy group, etc.), a sulfamoyl group (for example, an N-ethylsulfamoyl group, an N-octadecylsulfamoyl group, etc.), a carbamoyl group (for example, an N-ethylcarbamoyl group, an N-methyl-N-dodecylcarbamoyl group, etc.), an acylamino group (for example, an acetylamino group, a benzamido group, etc.), a diacylamino group (for example, a succinimido group, a hydantoinyl group, etc.), a ureido group (for example, a methylureido group, a phenylureido group, a (4-methoxyphenyl)ureido group, etc.), an N-alkylanilino group (for example, an N-methylanilino group, an N-butylanilino group, etc.), an N-acylanilino group (for example, an N-acetylanilino group, an N-trichloroacetylanilino group, etc.), a hydroxy group, and a mercapto group. n in the general formula (II) represents 0 or an integer from 1 to 3, and when n is 2 or more, the groups represented by R may be the same or different.

In the general formula (II), X represents a divalent connecting group. More particularly, X represents a divalent group selected from an alkylene group preferably having from 1 to 22 carbon atoms (for example, a methylene group, a cyclohexylene group, etc.), a phenylene group, a naphthylene group, an ether group, an amino group, a carbonyl group, a thioether group and a sulfone group or a divalent group comprising a combination of these divalent groups. The carbon atom and the nitrogen atom in the divalent connecting group may be substituted.

More preferred couplers used in the present invention are those wherein Q in the general formula (I) represents a 3-anilino-5-pyrazolone type magenta color forming coupler residue and a methylenedioxybenzene derivative is connected to the non-coupling position thereof and represented by the following general formula (III):

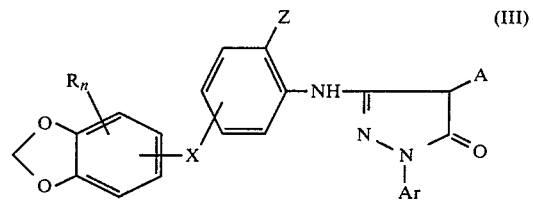

wherein X, R and n each has the same meaning as defined above.

In the general formula (III), Z represents a halogen atom (for example, a chlorine atom, a bromine atom, etc.) or an alkoxy group having 1 to 22 carbon atoms (for example, a methoxy group, an ethoxy group, a heptoxy group, a tetradecyloxy group, a hexadecyloxy group, an octadecyloxy group, a dodecyloxy group, an allyloxy group, a benzyloxy group, a phenethyloxy group, etc.). The alkoxy group can be substituted with one or more substituents selected from a halogen atom, a nitro group, a cyano group, an alkoxy group (for example, a methoxy group, an ethoxy group, etc.), an arylxoy group (for example, a phenyloxy group, a naphthyloxy group, etc.), an alkylcarbonyl group (for example, an acetyl group, a tetradecanoyl group, etc.), an alkoxycarbonyl group (for example, a methoxycarbonyl group, a benzyloxycarbonyl group, etc.), an acylamino group (for example, an acetylamino group, a benzamido group, etc.), a sulfonamido group (for example, a methanesulfonamido group, a p-toluenesulfonamido group, etc.), a hydroxy group and a mercapto group. Where Z is an alkoxy group substituted with a fluorine atom, Z can also be a so-called polyfluoroalkoxy group.

In the general formula (III), A represents a hydrogen atom or a coupling-off group. Suitable coupling-off groups represented by A include, for instance, a thiocyano group, an acyloxy group preferably having from 2 to 22 carbon atoms (for example, an acetoxy group, a dodecanoyloxy group, an octadecanoyloxy group, a 3-pentadecylphenoxyacetoxy group, a benzoyloxy group, a β-naphthoyloxy group, a 3-[γ-(2,4-di-tert-amylphenoxy)butyramido]benzyloxy group, etc.), an aryloxy group preferably having from 6 to 22 carbon atoms (for example, a phenoxy group, a p-chlorophenoxy group, a p-nitrophenoxy group, a naphthoxy group, etc.), an alkoxy group preferably having from 1 to 22 carbon atoms (for example, a methoxy group, etc.), a halogen atom (for example, a chlorine atom, a fluorine atom, etc.), an arylazo group preferably having from 6 to 22 carbon atoms (for example, a phenylazo group, a 2-methyl-4-hydroxyphenylazo group, a naphthylazo group, etc.), an aryltriazolyl group preferably having from 6 to 22 carbon atoms (for example, a 1-benzotriazolyl group, a 2-benzotriazolyl group, a 2-naphthotriazolyl group, etc.), an alkylthio group preferably having from 1 to 22 carbon atoms (for example, a hexylthio group, a dodecylthio group, etc.), an arylthio group preferably having from 6 to 22 carbon atoms (for example, a phenylthio group, a naphthylthio group, a 2-butyloxy-5-t-octyl-phenylthio group, etc.), an aralkoxycarbonyloxy group preferably having from 8 to 22 carbon atoms (for example, a benzyloxycarbonyloxy group, etc.), an alkoxycarbonyloxy group preferably having from 2 to 22 carbon atoms (for example, a methoxycarbonyloxy group, etc.), an aryloxycarbonyloxy group preferably having from 7 to 22 carbon atoms (for example, a phenoxycarbonyloxy group, etc.), a heterocyclic thio group (for example, a 2-benzothiazolylthio group, a 1-phenyl-5-tetrazolylthio group, a 2-benzoxazolylthio group, a 2-benzimidazolylthio group, a 5-phenyl-1,3,4-oxadiazolyl-2-thio group, etc.), a cycloalkylthio group preferably having from 4 to 22 carbon atoms, more preferably from 6 to 22 carbon atoms (for example, a cyclohexylthio group, etc.), a cycloalkoxy group preferably having from 4 to 22 carbon atoms, more preferably from 6 to 22 carbon atoms (for example, a cyclohexyloxy group, etc.), an imido group (for example, a phthalimido group, a succinimido group, a 5,5-dimethyl-3-hydantoinyl group, a 5,5-dimethyl-3-oxazolidinyl group, etc.), an imidazolyl group (for example, a 1-imidazolyl group, a 2-methyl-1-imidazolyl group, a 1-benzimidazolyl group, etc.), a pyrazolyl group (for example, 1-pyrazolyl group, a 4-chloro-1-pyrazolyl group, etc.), a triazolyl group (for example, a 3,5-dimethyl-1,2,4-triazol-1-yl group, a 3,5-diethyl-1,2,4-triazol-1-yl group, etc.), an acylamino group preferably having from 2 to 22 carbon atoms (for example, a benzamido group, an acetylamino group, etc.), a sulfonamido group preferably having from 1 to 22 carbon atoms (for example, a benzenesulfonamido group, a methanesulfonamido group, etc.), a cycloamino group preferably having up to 22 carbon atoms (for example, a piperidino group, a morpholino group, etc.), or the like.

In the general formula (III), Ar represents an aryl group preferably having from 6 to 22 carbon atoms (for example, a phenyl group, a 2-chlorophenyl group, a 4-chlorophenyl group, a 2,5-dichlorophenyl group, a 2,6-dichlorophenyl group, a 2,4,6-trichlorophenyl group, a 2-bromophenyl group, a 3,5-dibromophenyl group, a 2-cyanophenyl group, a 2,6-dichloro-4-cyanophenyl group, a 4-cyanophenyl group, a 4-methylphenyl group, a 2,6-dimethylphenyl group, a 4-butylphenyl group, a 2-trifluoromethylphenyl group, a 2-ethoxyphenyl group, an N-methylbenzamidophenyl group, an N,N-diphenylsulfamoylphenyl group, a phenyl-N-methylsulfonamidophenyl group, a 2,6-dichloro-4-[α-(2,4-di-tert-amylphenoxy)butanamido]phenyl group, a 2,6-dichloro-4-tetradecyloxycarbonylphenyl group, a 2,6-dichloro-4-octadecyloxyphenyl group, a 2,6-dichloro-4-hexadecylthiophenyl group, a 2,6-dichloro-4-octadecylsulfonylphenyl group, a 2,3,4,5,6-pentafluorophenyl group, a 2,3,4,5,6-pentachlorophenyl group, a 2-chloro-5-cyanophenyl group, a 5-chloro-2-methylphenyl group, a 2,6-dichloro-4-methylphenyl group, a 2,4-dichloro-6-methylphenyl group, a 2-chloro-4,6-dimethylphenyl group, a 2,6-dichloro-4-methoxyphenyl group, a 2,6-dichloro-4-methoxycarbonylphenyl group, etc.).

The magenta color image forming couplers according to the present invention are novel couplers. It is surprising that the fastness of color images formed from the couplers to light irradiation is extremely good in comparison with the case wherein a methylenedioxy compound is used in a combination with a magenta color image forming coupler as described in Japanese Patent Application (OPI) No. 52747/81 (corresponding to U.S. Pat. No. 4,332,886) (the term "OPI" as used herein refers to a "published unexamined Japanese patent application").

Specific examples of the magenta color image forming couplers which can be employed in the present invention are shown below, but the present invention is not to be construed as being limited thereto.

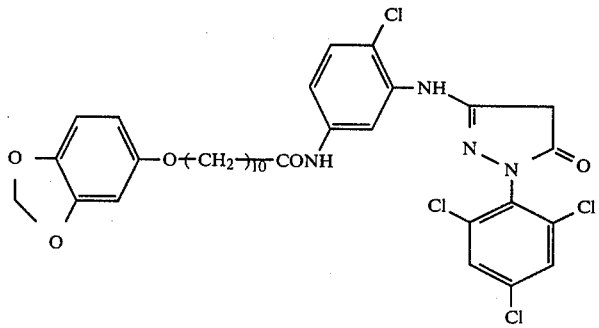

Coupler (1)

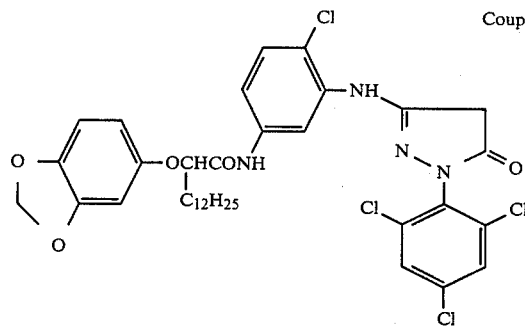

Coupler (2)

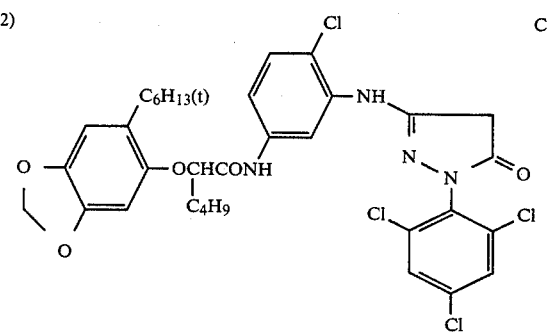

Coupler (3)

-continued
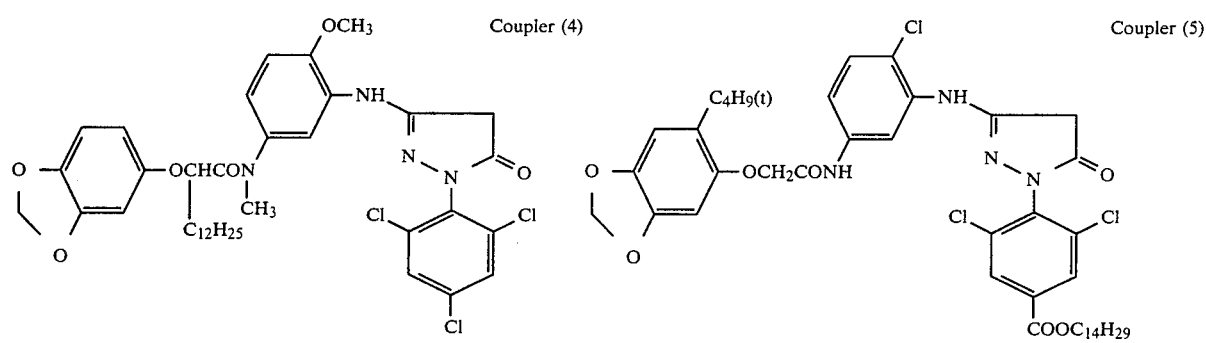
Coupler (4)
Coupler (5)
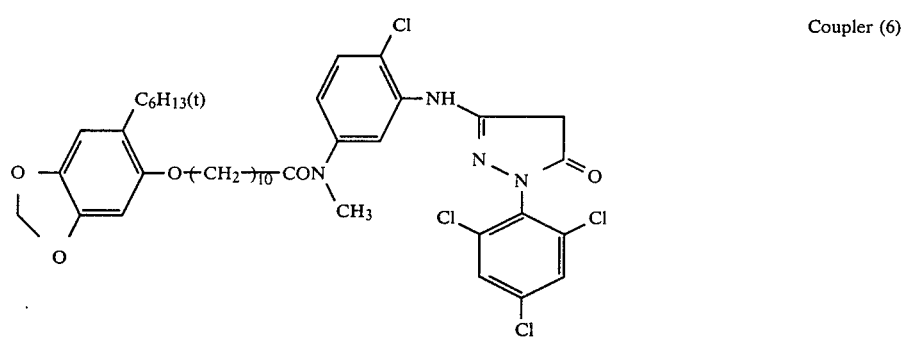
Coupler (6)
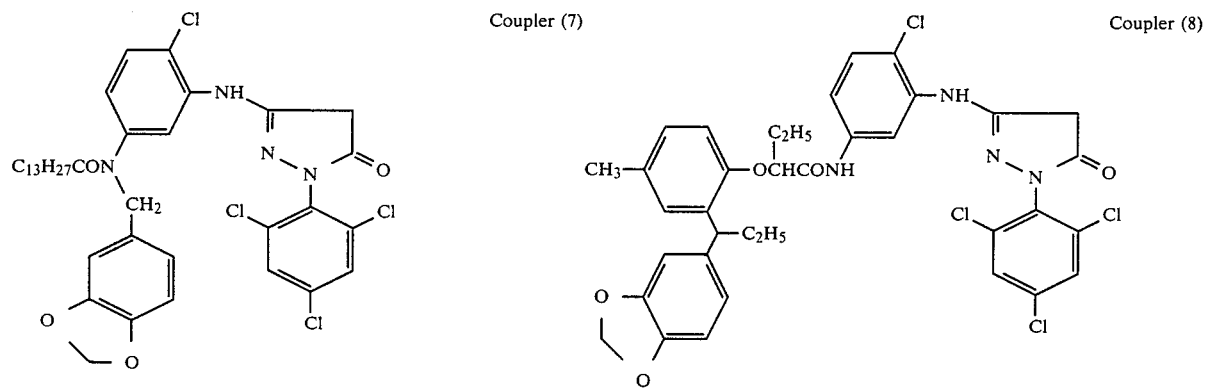
Coupler (7)
Coupler (8)
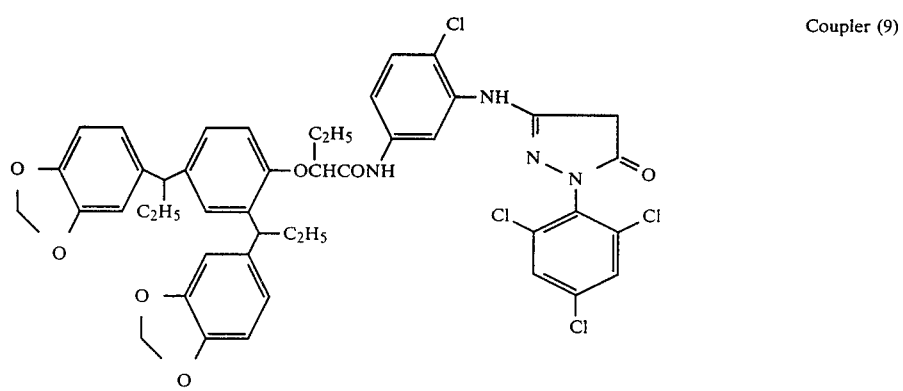
Coupler (9)

Coupler (10)
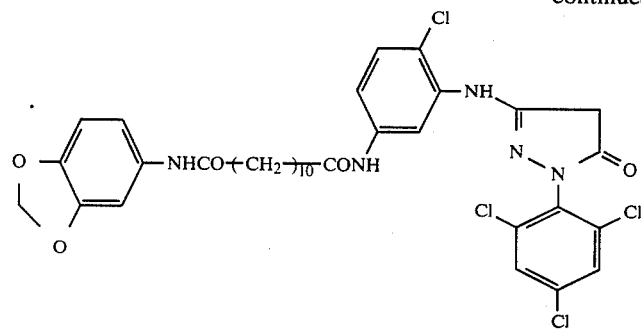
Coupler (11)                                              Coupler (12)
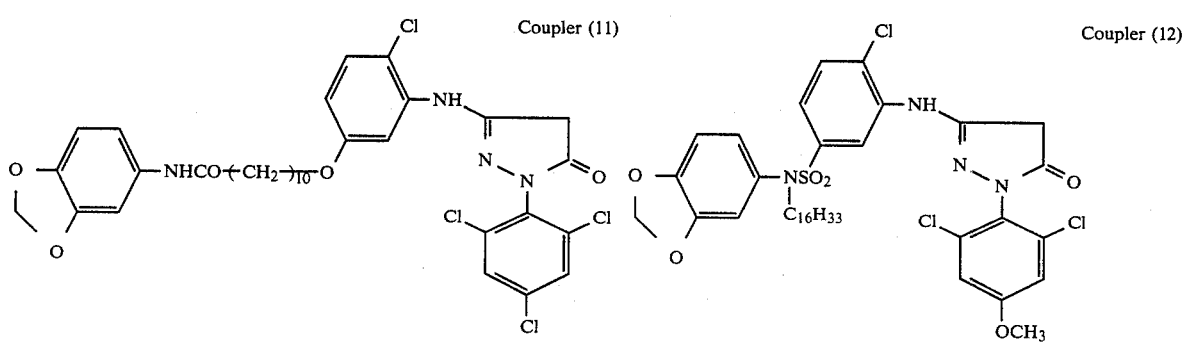
Coupler (13)
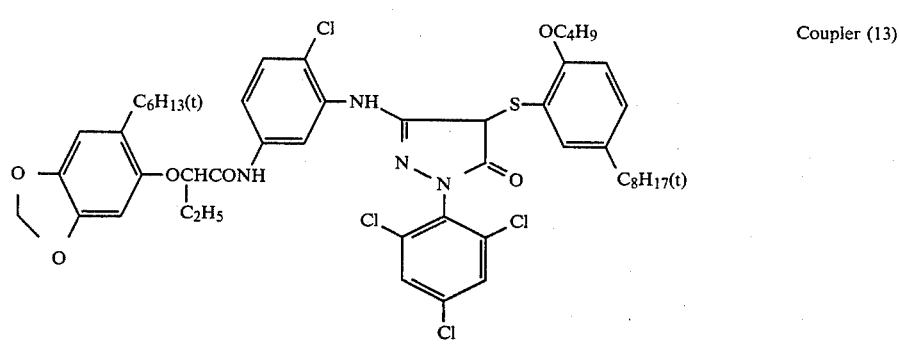
Coupler (14)                                              Coupler (15)
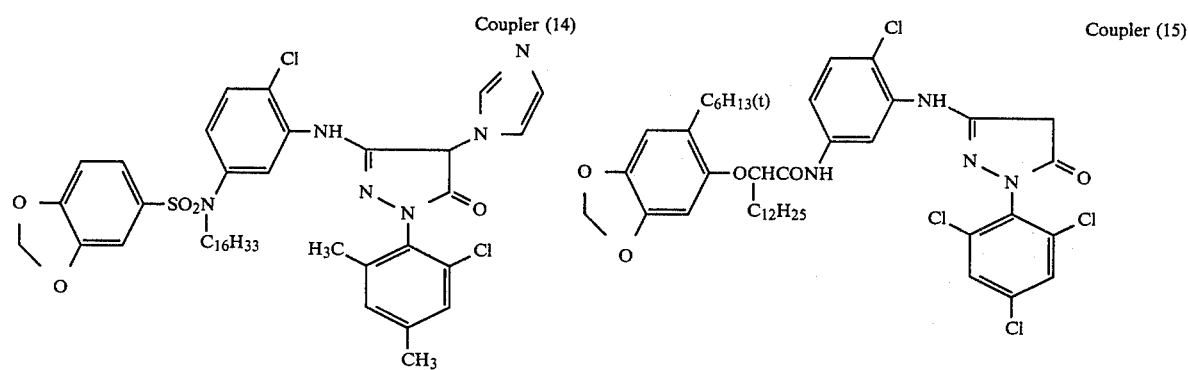
Coupler (16)                                              Coupler (17)
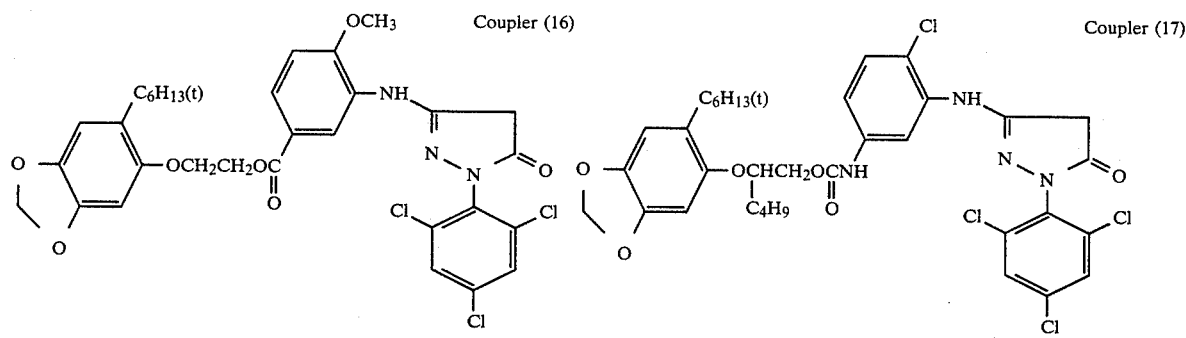

-continued
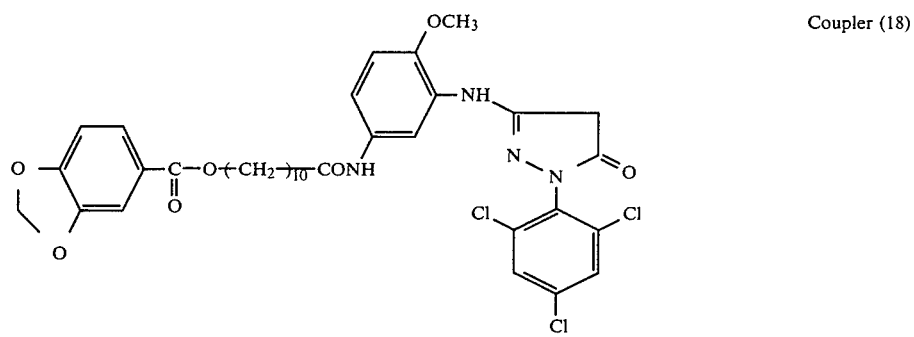
Coupler (18)
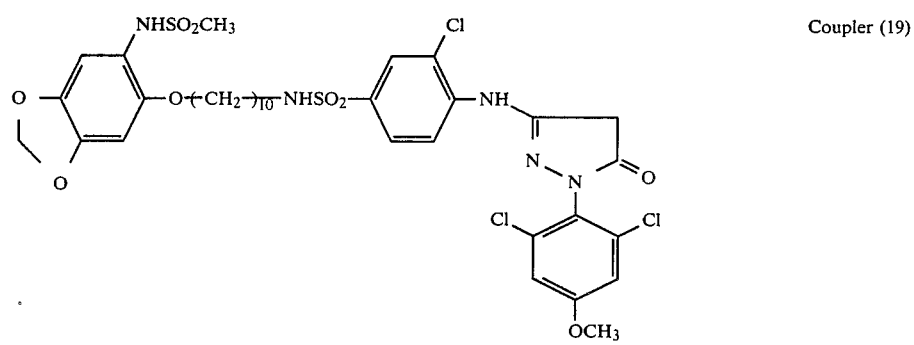
Coupler (19)
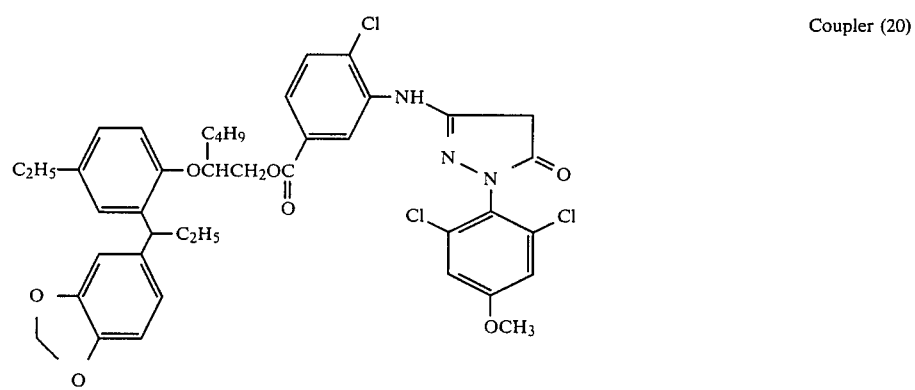
Coupler (20)
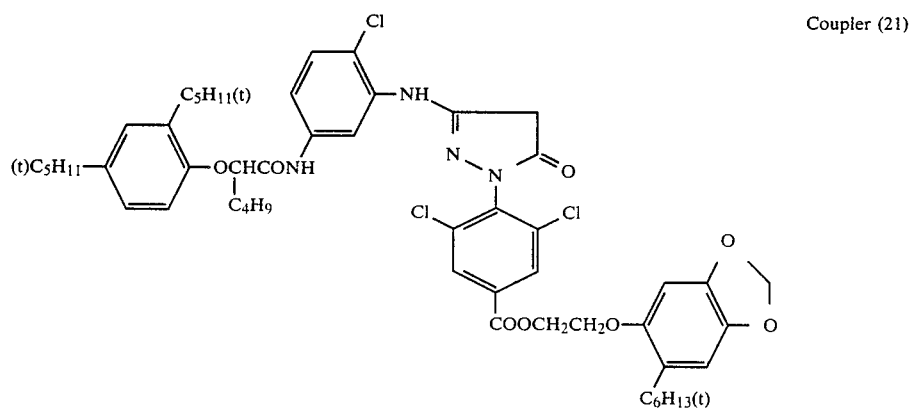
Coupler (21)

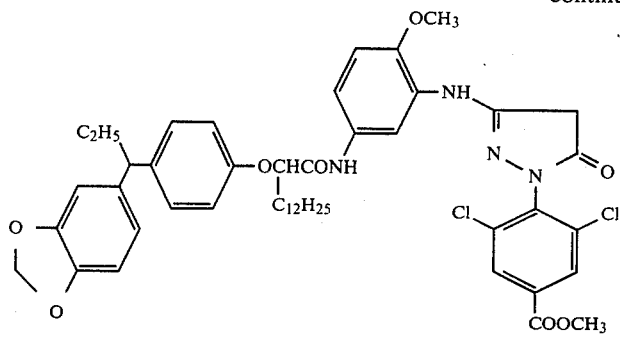
Coupler (22)
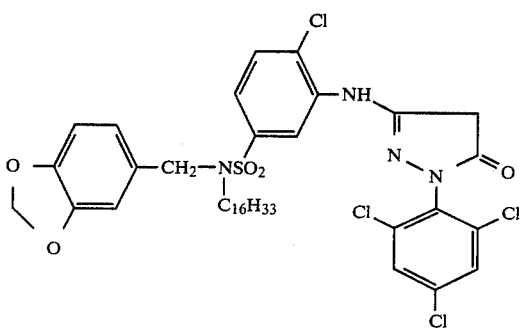
Coupler (23)
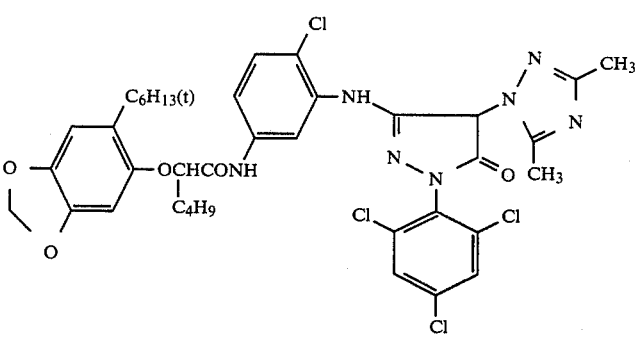
Coupler (24)
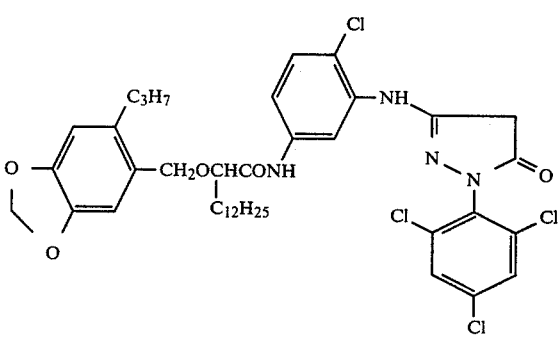
Coupler (25)
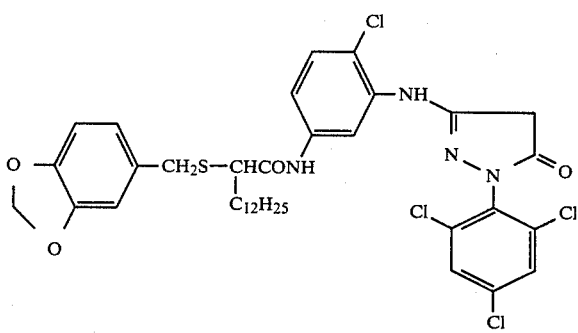
Coupler (26)

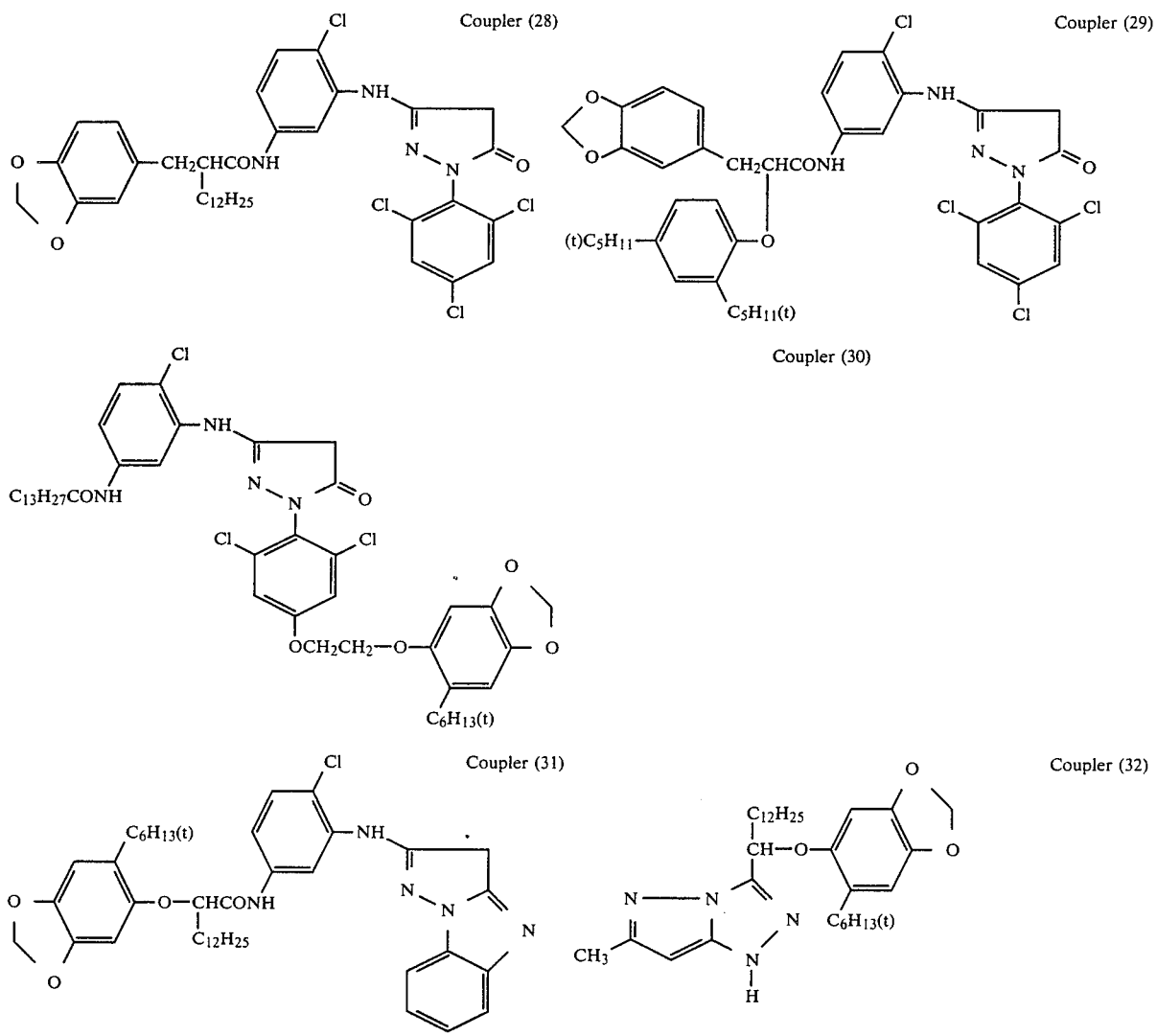

A specific synthesis example for a representative magenta color forming coupler according to the present invention is illustrated below.

SYNTHESIS EXAMPLE 1

Synthesis of 1-(2,4,6-Trichlorophenyl)-3-{2-chloro-5-[2-(3,4-methylenedioxyphenoxy)tetradecanamidol]}anilino-5-pyrazolone [Coupler (2)]

Step (1): Synthesis of 2-(3,4-methylenedioxyphenoxy)tetradecanoic acid:

33.5 g of 2-bromotetradecanoic acid ethyl ester and 13.8 g of 3,4-methylenedioxyphenol were dissolved in 100 ml of dimethylformamide, to which was added 13.8 g of anhydrous potassium carbonate while introducing a nitrogen gas and the mixture was stirred at 90° C. for 6 hours. The reaction solution was poured into 300 ml of cold water and extracted with 300 ml of ethyl acetate. The ethyl acetate layer was washed with 300 ml of water and the ethyl acetate was distilled off under reduced pressure. To the residue was added 120 ml of a 10% methanol solution of potassium hydroxide and the mixture was refluxed for 30 minutes. The reaction mixture was poured into 300 ml of a cold 7% aqueous hydrochloric acid solution and extracted with 300 ml of ethyl acetate. The ethyl acetate layer was washed with 300 ml of water and dried with anhydrous sodium sulfate. After removing the sodium sulfate by filtration, the ethyl acetate was distilled off under reduced pressure and to the resulting residue was added 70 ml of acetonitrile to crystallize. The crystals thus deposited were collected by filtration to obtain 40 g of 2-(3,4-methylenedioxyphenoxy)tetradecanoic acid having a melting point of 70° to 72° C.

Step (2): Synthesis of Coupler (2):

36.4 g of 2-(3,4-methylenedioxyphenoxy)tetradecanoic acid was dissolved in 200 ml of benzene and to the solution was added dropwise 8 ml of thionyl chloride under reflux over a period of 10 minutes. After further refluxing for 30 minutes, the benzene and the excess thionyl chloride were distilled off under reduced pressure to obtain an oily product. To 40 g of 1-(2,4,6-trichlorophenyl)-3-(2-chloro-5-aminoanilino)-5-pyrazolone was added 400 ml of acetonitrile and the mixture was stirred with heating on a steam bath, to which was added dropwise the above described oily product over a period of 20 minutes. After further stirring with heating for 1 hour, the reaction mixture was poured into 500 ml of ice water and extracted with 500 ml of ethyl acetate. The ethyl acetate layer was washed with an aqueous sodium hydrogencarbonate solution, then twice with 500 ml of water and dried with anhydrous sodium sulfate. After removing the sodium sulfate by filtration, the ethyl acetate was distilled off under reduced pressure and the residue was crystallized with a solvent mixture of methanol/ethanol/ethyl acetate. The crystals were collected by filtration and recrystallized from the same solvent mixture as described above to obtain 30 g of Coupler (2). Melting point was 132° to 135° C.

Elemental Analysis: Calculated (%): C: 57.61, H: 5.37, N: 7.46; Found (%): C: 57.43, H: 5.23, N: 7.35.

Other couplers can also be synthesized in a manner similar to Synthesis Example 1 as above. For example, a melting point of Coupler (1) was 70° to 75° C., a melting point of Coupler (3) was 208° to 210° C., a melting point of Coupler (8) was 115° to 120° C., a melting point of Coupler (15) was 119° to 121° C., and Coupler (27) was semi-solid (at room temperature).

The coupler of the general formula (I) according to the present invention is incorporated into the emulsion layer, generaly in an amount of from $2 \times 10^{-3}$ mol to $5 \times 10^{-1}$ mol, preferably $1 \times 10^{-2}$ mol to $5 \times 10^{-1}$ mol, per mol of silver.

The coupler in accordance with the present invention possesses both high coupling activity and sufficient solubility in an organic solvent, and, therefore, a color photographic material prepared using this coupler provides desirable photographic properties, such as a good sensitivity, gradation and the like, and possesses the characteristic that the photographic material is easy to prepare. Moreover, the color photographic material has the characteristics that not only does the photographic color image obtained by the development processing thereof possess a spectral absorption characteristic which is advantageous for color reproduction and sufficient light fastness, but also, after color development processing, yellow stain is reduced in the unexposed portions, and increase in the yellow stain is minimal even on exposure to light for a long period of time. Furthermore, fading of the photographic color images due to light irradiation is greatly reduced.

Furthermore, the color image obtained from the coupler in accordance with the present invention is resistant to the adverse actions of heat and humidity.

In order to prepare a silver halide color photographic light-sensitive material using the coupler according to the present invention, the coupler according to the present invention can be used individually, two or more couplers according to the present invention can be used as a mixture thereof, or the coupler according to the present invention can be used in combination with a coupler other than the coupler according to the present invention.

Conventional magenta color forming couplers which can be used together with the magenta color forming coupler of the general formula (I) according to the present invention include pyrazolone type compounds, indazolone type compounds, cyanoacetyl type compounds, etc., and pyrazolone type compounds are particularly preferred. Specific examples of such magenta color forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78, and so forth.

Known open chain ketomethylene type couplers can be used as yellow color forming couplers in the color photographic light-sensitive material according to the present invention. Of these couplers, benzoyl acetanilide type and pivaloyl acetanilide type compounds are especially effective. Specific examples of yellow color forming couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Patent No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77, and so forth.

Phenol type compounds, naphthol type compounds, etc., can be employed as cyan color forming couplers. Specific examples of cyan color forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 69624/77 and 90932/77, and so forth.

Colored couplers which can be employed are described, for example, in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, West German Patent Application (OLS) No. 2,418,959, etc.

Development inhibitor releasing (DIR) couplers which can be employed are described, for example, in U.S. Pat. Nos. 3,227,554, 3,617,291, 3,701,783, 3,790,384 and 3,632,345, West German Patent Application (OLS)

Nos. 2,414,006, 2,454,301 and 2,454,329, British Patent No. 953,454, Japanese Patent Application (OPI) Nos. 69624/77, 122335/74, Japanese Patent Publication No. 16141/76, etc.

In addition to DIR couplers, other compounds which release development inhibitors upon development can also be present in the light-sensitive material. For example, DIR compounds as described, for example, in U.S. Pat. Nos. 3,297,445 and 3,379,529, West German Patent Application (OLS) No. 2,417,914, Japanese Patent Application (OPI) Nos. 15271/77 and 9116/78, etc., can be employed.

Two or more kinds of the couplers described above can be incorporated in the same layer or the same coupler compound can also be present in two or more layers.

Conventional methods, e.g., the method described in U.S. Pat. No. 2,322,027, can be employed to incorporate the coupler into the silver halide emulsion layer. For example, the coupler can be dissolved either in an organic solvent having a high boiling point such as phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate, etc.), citric acid esters (e.g., tributyl acetylcitrate, etc.), benzoic acid esters (e.g., octyl benzoate, etc.), alkyl amides (e.g., diethyl laurylamide, etc.), fatty acid esters (e.g., dibutoxyethyl succinate, dioctyl azelate, etc.), etc.; or an organic solvent having a relatively low boiling point of from about 30° to 150° C. such as a lower alkyl acetate (e.g., ethyl acetate, butyl acetate, etc.), ethyl propionate, sec-butyl alcohol, methyl isobutyl ketone, β-ethoxyethyl acetate, methyl Cellosolve acetate, etc. Then, the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 can also be used.

When couplers having an acid group, such as a carboxylic acid group, a sulfonic acid group, etc., are used, they can be incorporated in a hydrophilic colloid as an alkaline aqueous solution thereof.

The photographic emulsion used in the present invention can be prepared using the methods described in, e.g., P. Glafkides, *Chimie et Physique Photographique*, Paul Montel (1967), G. F. Duffin, *Photographic Emulsion Chemistry*, The Focal Press (1966), V. L. Zelikman, et al., *Making and Coating Photographic Emulsions*, The Focal Press (1964), etc. That is, any of the acid method, the neutral method, the ammonia method and other methods can be used. Moreover, a soluble silver salt can be reacted with a soluble halogen salt using any of the single jet method, the double jet method and a combination thereof.

A method in which grains are formed in the presence of an excess of silver ions (i.e., the socalled reverse mixing method) can also be used. As one of the modes of the double jet method, the method in which the pAg of the liquid phase in which the silver halide is to be produced is kept constant, that is, the so-called controlled double jet method, can be used. This method can provide silver halide emulsions having a regular crystal form and an almost uniform grain size.

Two or more silver halide emulsions which are separately prepared can be mixed and then used, if desired.

In the process of the formation of the silver halide grains or physical ripening, cadmium salts, zinc salts, lead salts, thallium salts, iridium salts or complex salts thereof, rhodium salts or complex salts thereof, iron salts or iron complex salts, and the like can be present.

Gelatin can advantageously be used as the binder or protective colloid for the photographic emulsion used in the present invention. However, other hydrophilic colloids can be used as well. For example, proteins such as gelatin derivatives, graft polymers between gelatin and other high polymers, albumin, casein, etc.; cellulose derivatives such as hydroxyethyl cellulose, carboxymethyl cellulose, cellulose sulfates, etc.; saccharide derivatives such as sodium alginate, starch derivatives, etc.; and various synthetic hydrophilic high polymers of homo- or copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used as the binder or protective colloid for the photographic emulsion.

Acid-processed gelatin and enzyme-processed gelatin as described in *Bull. Soc. Sci. Photo. Japan*, No. 16, p. 30 (1966) can be used as well as lime-processed gelatin as the gelatin component. In addition, the hydrolyzed products of gelatin and enzyme-decomposed products of gelatin are also suitable. Suitable gelatin derivatives which can be used include those obtained by reacting gelatin with various compounds, such as acid halides, acid anhydrides, isocyanates, bromoacetic acid, alkanesultones, vinylsulfonamides, maleinimide compounds, polyalkylene oxides, epoxy compounds, etc. Specific examples thereof are described in U.S. Pat. Nos. 2,614,928, 3,132,945, 3,186,846 and 3,312,553, British Pat. Nos. 861,414, 1,033,189 and 1,005,784, Japanese Patent Publication No. 26845/67, etc.

As the above-described gelatin graft polymer, those which are obtained by grafting homo- or copolymers of vinyl monomers such as acrylic acid, methacrylic acid, the ester or amide derivatives thereof, acrylonitrile, styrene, etc., to gelatin can be used. In particular, graft polymers with a polymer having some compatibility with gelatin, such as polymers of acrylic acid, methacrylic acid, acrylamide, methacrylamide, hydroxyalkyl methacrylates, etc., are preferred. Examples thereof are described in U.S. Pat. Nos. 2,763,625, 2,831,767 and 2,956,884, etc. Typical synthetic hydrophilic materials are described in, e.g., West German Patent Application (OLS) No. 2,312,708, U.S. Pat. Nos. 3,620,751 and 3,879,205 and Japanese Patent Publication No. 7561/68, etc.

For the purposes of preventing fog or stabilizing the photographic properties during preparation, storage, and/or photographic processing of light-sensitive material, a variety of compounds can be incorporated into photographic emulsions used according to the present invention. For example, a wide variety of compounds which are known as anti-fogging agents or stabilizers, such as azoles, e.g., benzothiazolium salts, nitroindazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole), etc.; mercaptopyrimidines; mercaptotriazines; thioketo compounds, such as oxazolinethione; azaindenes, e.g., triazaindenes, tetraazaindenes (especially 4-hydroxy-substituted (1,3,3a,7)tetraazaindenes), pentaazaindenes, etc.; benzenethiosulfonic acid, benzenesulfinic acid, benzenesulfonic acid amide, etc., can be used. For example, the compounds as described in U.S. Pat. Nos. 3,954,474 and 3,982,947, Japanese Patent Publication No. 28660/77 can be used.

For the purpose of increasing sensitivity, increasing contrast, or accelerating development, photographic emulsion layer of the photographic lightsensitive material according to the present invention can contain other known additives, such as, for example, polyalkylene oxides or derivatives thereof such as ethers, esters, amines, etc., thioether compounds, thiomorpholine compounds, quaternary ammonium compounds, urethane derivatives, urea derivatives, imidazole derivatives, 3-pyrazolidones, etc. For example, such additives as described in U.S. Pat. Nos. 2,400,532, 2,423,549, 2,716,062, 3,617,280, 3,772,021 and 3,808,003, British Pat. No. 1,488,991, etc.

The photographic emulsion layers and other hydrophilic colloid layers of the light-sensitive material prepared in accordance with the present invention can contain whitening agents, such as stilbenes, triazines, oxazoles, or coumarins, etc. These agents can be water-soluble or can also be employed as a dispersion of water-insoluble whitening agents. Specific examples of fluorescent whitening agents are described in U.S. Pat. Nos. 2,632,701, 3,269,840 and 3,359,102, and British Pat. Nos. 852,075 and 1,319,763, etc.

The hydrophilic colloid layers of the light-sensitive material prepared according to the present invention can contain water-soluble dyes such as filter dyes or for purpose of preventing irradiation or other various purposes. Such dyes include oxonol dyes, hemioxonol dyes, styryl dyes, merocyanine dyes, cyanine dyes and azo dyes. Of these dyes, oxonol dyes, hemioxonol dyes and merocyanine dyes are especially useful. Specific examples of such dyes which can be employed are described, for example, in British Pat. Nos. 584,609 and 1,177,429, Japanese Patent Application (OPI) Nos. 85130/73, 99620/74, 114420/74 and 108115/77, U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352, etc.

The photographic emulsion used in the present invention can also be spectrally sensitized with methine dyes of other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes, such as basic heterocyclic nuclei, is applicable to these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by condensing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei can also be substituted.

The merocyanine dyes and the complex merocyanine dyes that can be employed contain 5- or 6-membered heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, and so forth.

Useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, Japanese Patent Publication Nos. 14030/69 and 24844/77, and so forth.

These sensitizing dyes can be employed individually, and can also be employed in combination. A combination of sensitizing dyes is often used particularly for the purpose of supersensitization.

Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, Japanese Patent Publication Nos. 4936/68 and 12375/78, and Japanese Patent Application (OPI) Nos. 110618/77 and 109925/77.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic ring group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present. The combinations described in U.S. Pat. Nos. 3,615,613, 3,615,641, 3,617,295 and 3,635,721 are particularly useful.

The present invention is also applicable to a multilayer multicolor photographic material containing layers sensitive to at least two different spectral wavelength ranges on a support. A multilayer natural color photographic material generally possesses at least one red-sensitive silver halide emulsion layer, at least one green-sensitive silver halide emulsion layer and at least one blue-sensitive silver halide emulsion layer, respectively, on a support. The order of these layers can be varied, if desired. Ordinarily, a cyan forming coupler is present in a red-sensitive emulsion layer, a magenta forming coupler is present in a green-sensitive emulsion layer and a yellow forming coupler is present in a blue-sensitive emulsion layer, respectively. However, if desired, a different combination can be employed.

Light-sensitive materials prepared according to the present invention can also contain, as color fog preventing agents, hydroquinone derivatives, aminophenol derivatives, gallic acid derivatives, ascorbic acid derivatives, or the like. Specific examples of these agents are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese Patent Application (OPI) Nos. 92988/75, 92989/75, 93928/75, 110337/75 and 146235/77, Japanese Patent Publication No. 23813/75, and so forth.

The hydrophilic colloid layers of the light-sensitive materials prepared in accordance with the present invention can also contain UV absorbents. For example, benzotriazole compounds substituted with aryl groups (e.g., those described in U.S. Pat. No. 3,533,794), 4-tiazolidone compounds (e.g., those described in U.S. Pat. Nos. 3,314,794 and 3,352,681), benzophenone compounds (e.g., those described in Japanese Patent Application (OPI) No. 2784/71), cinnamic acid ester compounds (e.g., those described in U.S. Pat. Nos. 3,707,375 and 3,705,805), butadiene compounds (e.g., those described in U.S. Pat. No. 4,045,229) or benzoxazole compounds (e.g., those described in U.S. Pat. No. 3,700,455) can be employed. Furthermore, the compounds as described in U.S. Pat. No. 3,499,762, Japanese Patent Application (OPI) No. 48535/79 can also be used. UV absorbing couplers (e.g., α-naphthol type cyan color forming couplers) and UV absorbing polymers can also be employed. These UV absorbents can also be mordanted in a specific layer(s), if desired.

In the practice of the present invention, known color fading preventing agents as described below can be employed. These fading preventing agents can be used individually or in a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Patent No. 1,363,921; gallic acid derivatives as described in U.S. Pat. Nos. 3,457,079 and 3,069,262; p-alkoxyphenols as described in U.S. Pat. Nos. 2,735,765 and 3,698,909, Japanese Patent Publication Nos. 20977/74 and 6623/77; p-oxyphenol derivatives as described in U.S. Pat. Nos. 3,432,300, 3,573,050, 3,574,627 and 3,764,337, Japanese Patent Application (OPI) Nos. 35633/77, 147434/77 and 15222/77; bisphenol derivatives as described in U.S. Pat. No. 3,700,455, etc.

Known methods can be used for processing the light-sensitive material according to the present invention. Known processing solutions can be used. The processing temperature can be from 18° C. to 50° C., in general, but temperatures lower than about 18° C. or higher than about 50° C. may be used, if desired. Either a development processing for forming silver images (black-and-white photographic processing) or a color photographic processing comprising developing processing for forming dye images can be employed, if desired.

Among methods that can be employed are a negative-positive method (for example, as described in *Journal of the Society of Motion Picture and Television Engineers*, Vol. 61, pages 667 to 701 (1953); a color reversal method which comprises developing with a developer containing a black-and-white developing agent to form a negative silver image, then subjecting the photographic material to at least one uniform exposure or to another appropriate fogging treatment, and subsequently performing color development to obtain positive dye images; and a silver dye bleaching method which comprises exposing a dye-containing photographic emulsion layer and developing the same to form a silver image and then bleaching the dyes using the silver image as a bleaching catalyst.

The color developing solution generally comprises an alkaline aqueous solution containing a color developing agent. Suitable color developing agents which can be employed include known primary aromatic amine developing agents, e.g., phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfamidoethylaniline, 4-amino-3-methyl-N-ethyl-N-β-methoxyethylaniline, etc.).

In addition, developing agents as described in L. F. A. Mason, *Photographic Processing Chemistry*, pages 226 to 229, Focal Press (1966), U.S. Pat. Nos. 2,193,015 and 2,592,364, Japanese Patent Application (OPI) No. 64933/73, etc., can be employed.

The color developing solution can also contain pH buffering agents, such as sulfites, carbonates, borates and phosphates of alkali metals, developing inhibitors or anti-fogging agents such as bromides, iodides or organic anti-fogging agents, etc. In addition, if desired, the color developing solution can also contain water softeners, preservatives such as hydroxylamine; organic solvents such as benzyl alcohol, diethylene glycol, etc.; developing accelerators such as polyethylene glycol, quaternary ammonium salts, amines; dye forming couplers; competing couplers; fogging agents such as sodium borohydride; auxiliary developing agents such as 1-phenyl-3-pyrazolidone; viscosity-imparting agents; polycarboxylic acid type chelating agents described in U.S. Pat. No. 4,083,723; anti-oxidizing agents as described in West German Patent Application (OLS) No. 2,622,950; and the like.

The photographic emulsion layers after color development are generally subjected to bleach processing. Bleach processing can be performed at the same time as fixing, or separately therefrom. Suitable bleaching agents which can be employed are compounds of polyvalent metals such as iron (III), cobalt (III), chromium (VI), copper (II), etc., peracids, quinones, nitroso compounds, ec. Specific examples include ferricyanides; bichromates; organic complexes of iron (III) or cobalt (III) with aminopolycarboxylic acids such as ethylenediaminetetraacetic acid, nitrilotriacetic acid, 1,3-diamino-2-propanol tetraacetic acid, etc., or organic acids such as citric acid, tartaric acid, malic acid, etc.; persulfates; permanganates; nitrosophenol; etc. Of these, particularly useful bleaching agents are potassium ferricyanide, sodium ethylenediaminetetraacetate iron (III) and ammonium ethylenediaminetetraacetate iron (III). Ethylenediaminetetraacetate iron (III) complex is useful both in a bleaching solution and in a mono bath bleach-fixing solution.

Bleaching and bleach-fixing solutions can contain various additives, including bleach accelerating agents as described in U.S. Pat. Nos. 3,042,520 and 3,241,966, Japanese Patent Publication Nos. 8506/70 and 8836/70, thioether compounds as described in Japanese Patent Application (OPI) No. 65732/78, and the like.

The light-sensitive material prepared using the present invention may be subjected to processing with a developing solution which is replenished or otherwise maintains its properties by the methods as described in Japanese Patent Application (OPI) Nos. 84636/76, 119934/77, 46732/78, 9626/79, 19741/79 and 37731/79, etc.

The light-sensitive material prepared using the present invention may be processed with a bleach-fixing solution which can be subjected to regeneration treatment, such as by methods as described in Japanese Patent Application (OPI) Nos. 781/71, 49437/73, 18191/73, 145231/75, 18541/76, 19535/76 and 144620/76, Japanese Patent Publication No. 23178/76, etc.

The characteristics obtained by employing the magenta color forming coupler according to the present invention are more specifically explained with reference to the examples hereinafter, but the present invention should not be construed as being limited thereto. For comparison, the magenta couplers indicated below were used.

Comparison Coupler (a)

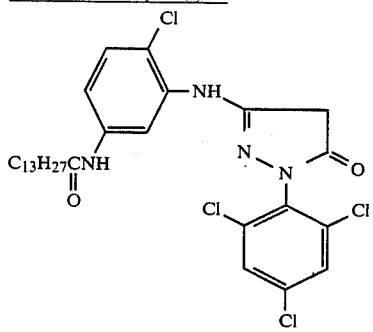

Comparison Coupler (b)

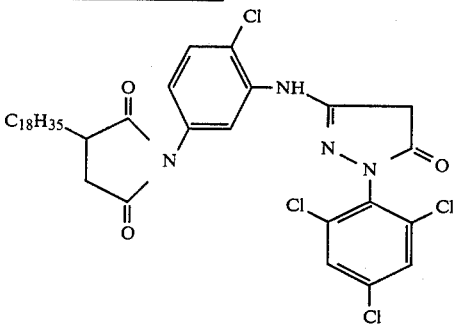

Comparison Coupler (c)

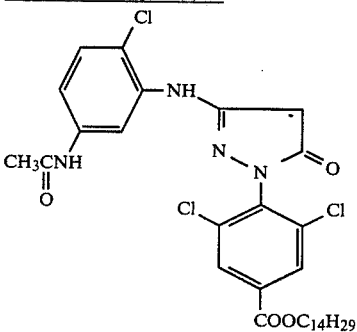

Comparison Couplers (a) and (c) are described in U.S. Pat. No. 3,935,015 and Comparison Coupler (b) is described in U.S. Pat. No. 3,684,514 and they are all known couplers.

EXAMPLE 1

10 g of Coupler (1) according to the present invention was dissolved in 10 ml of tricresyl phosphate and 10 ml of ethyl acetate and the solution was dispersed in 80 g of a 10% aqueous gelatin solution containing sodium dodecylbenzenesulfonate. Thus-prepared dispersion was mixed with 145 g of a green-sensitive silver chlorobromide emulsion (50 mol% silver bromide) containing 7 g of silver, and sodium dodecylbenzenesulfonate was added thereto as a coating aid. The mixture was coated on a paper support both surfaces of which were laminated with polyethylene and then a gelatin protective layer was coated at a coating amount of 1 g/m² on the emulsion layer and dried to prepare Sample (A).

Samples (B) to (K) were prepared in the same manner as described in the preparation of Sample (A) except that Couplers (2), (3), (5), (7), (8), (15) and (27) according to the present invention and Comparison Couplers (a), (b) and (c) described above were employed in place of Coupler (1), respectively.

These samples were exposed to light of 1,000 lux, 1 sec using a sensitometer and subjected to the following color development processing.

| Processing Step | Temperature (°C.) | Time |
|---|---|---|
| 1. Color Development | 33 | 3 min 30 sec |
| 2. Bleach-Fixing | 33 | 1 min 30 sec |
| 3. Washing with Water | 25 to 30 | 2 min 30 sec |

The processing solutions used had the following compositions.

| Color Developing Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 g |
| 4-Amino-N—ethyl-N—(β-methane-sulfonamidoethyl)-m-toluidine Sesquisulfate Monohydrate | 5 g |
| Adjust pH to 10.20 | |
| Water to make | 1 l |
| Bleach-Fixing Solution | |
| Ethylenediaminetetraacetic Acid | 2 g |
| Ferric Salt of Ethylenediaminetetraacetic Acid | 40 g |
| Sodium Sulfite | 5 g |
| Ammonium Thiosulfate | 70 g |
| Water to make | 1 l |

Each sample thus-processed with a dye image was subjected to fading testing for 2 weeks using a fluorescent lamp fading tester (20,000 lux) equipped with an ultraviolet light absorbing filter capable of absorbing substantially all ultraviolet lights having a wavelength of 400 nm or less (manufactured by Fuji Photo Film Co., Ltd.). The results obtained are shown in Table 1 below.

TABLE 1

| Sample | Coupler Used | Change of Yellow Stain Density in White Background* | Change of Magenta Density (initial density of 1.00) |
|---|---|---|---|
| (A) | Coupler (1) Present Invention | +0.04 | −0.12 |
| (B) | Coupler (2) Present Invention | +0.04 | −0.10 |
| (C) | Coupler (3) Present Invention | +0.03 | −0.08 |
| (D) | Coupler (5) Present Invention | +0.06 | −0.08 |
| (E) | Coupler (7) Present Invention | +0.05 | −0.14 |
| (F) | Coupler (8) Present Invention | +0.04 | −0.09 |
| (G) | Coupler (15) Present Invention | +0.03 | −0.08 |
| (H) | Coupler (27) Present Invention | +0.06 | −0.12 |
| (I) | Comparison | +0.17 | −0.53 |

TABLE 1-continued

| Sample | Coupler Used | Change of Yellow Stain Density in White Background* | Change of Magenta Density (initial density of 1.00) |
|---|---|---|---|
| (J) | Coupler (a) Comparison Coupler (b) | +0.14 | −0.47 |
| (K) | Comparison Coupler (c) | +0.20 | −0.56 |

*Yellow density in the white background before the fading test was 0.09 to 0.10 in each sample.

It is apparent from the results as shown in Table 1 that the couplers according to the present invention have extremely good light fastness.

EXAMPLE 2

In the same procedure as described in Example 1, Sample (L) in which Coupler (15) according to the present invention was used, Sample (M) in which Comparison Coupler (a) was used and Sample (N) in which Comparison Coupler (a) and Compound (e) described below in an amount of 50% by mol of Comparison Coupler (a) were used were prepared. Compound (e) is known as described in Japanese Patent Application (OPI) No. 52747/81 (corresponding to U.S. Pat. No. 4,332,886).

Compound (e)

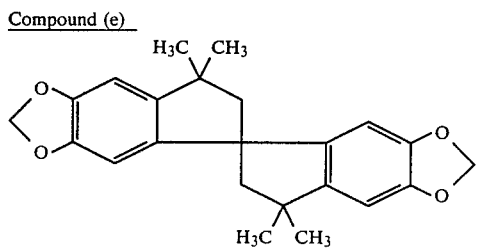

These samples were subjected to the same development processing as described in Example 1 and then to fading testing for 2 weeks using a fluorescent lamp fading tester (20,000 lux). The results obtained are shown in Table 2 below.

TABLE 2

| Sample | Coupler and Compound Used | Change of Yellow Stain Density in White Background* | Change of Magenta Density (initial density of 1.00) |
|---|---|---|---|
| (L) | Coupler (15) Present Invention | +0.03 | −0.06 |
| (M) | Comparison Coupler (a) | +0.17 | −0.53 |
| (N) | Comparison Coupler (a) and Compound (e) | +0.11 | −0.49 |

It is apparent from the results as shown in Table 2 that the coupler according to the present invention has extremely good light fastness in comparison with the case wherein the methylenedioxy compound is individually employed together with the coupler (equimolar amount of the methylenedioxy group per mol of coupler was used).

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive material comprising a support having thereon a silver halide emulsion layer containing therein a coupler represented by the following general formula (I):

wherein Q represents a coupler capable of forming a magenta color image upon the coupling reaction with an oxidation product of a developing agent which is a 3-anilino-5-pyrazolone type magenta color forming coupler residue; and B represents a group containing an unsubstituted or substituted methylenedioxybenzene group which is connected to a non-coupling position of Q.

2. A color photographic light-sensitive material as claimed in claim 1, wherein the coupler is represented by the following general formula (II):

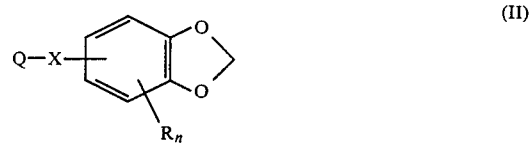

wherein Q represents a coupler residue capable of forming a magenta color image upon the coupling reaction with an oxidation product of a developing agent; R represents a straight chain, branched chain or cyclic alkyl group, an alkenyl group, an aralkyl group, a halogen atom, an alkoxy group or a hydroxy group, n represents 0 or an integer from 1 to 3, and when n is 2 or more, the groups represented by R may be the same or different; and X represents a divalent connecting group.

3. A color photographic light-sensitive material as claimed in claim 2, wherein the alkyl moiety or the aryl moiety included in the group represented by R are substituted with one or more substituents selected from a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, an acyloxy group, a sulfamoyl group, a carbamoyl group, an acylamino group, a diacylamino group, a ureido group, an N-alkylanilino group, an N-acylanilino group, a hydroxy group, and a mercapto group.

4. A color photographic light-sensitive material as claimed in claim 2, wherein X represents an alkylene group, a phenylene group, a naphthylene group, an ether group, an amino group, a carbonyl group, a thioether group, a sulfone group or a combination thereof.

5. A color photographic light-sensitive material as claimed in claim 2, wherein the coupler is represented by the following general formula (III):

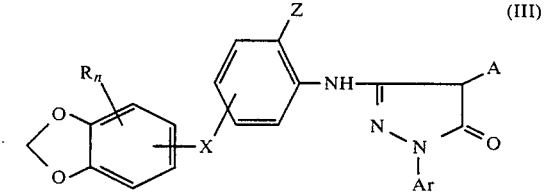

wherein X, R and n each has the same meaning as defined in claim 3, Z represents a halogen atom, or an alkoxy group having from 1 to 22 carbon atoms which may be substituted with one or more substituents selected from a halogen atom, a nitro group, a cyano group, an alkoxy group, an aryloxy group, an alkylcarbonyl group, an alkoxycarbonyl group, an acylamine group, a sulfonamido group, a hydroxy group, and a mercapto group; and Ar represents an aryl group.

6. A color photographic light-sensitive material as claimed in claim 5, wherein A represents a hydrogen atom.

7. A color photographic light-sensitive material as claimed in claim 5, wherein A represents a coupling-off group.

8. A color photographic light-sensitive material as claimed in claim 7, wherein A represents a thiocyano group, an acyloxy group, an aryloxy group, an alkoxy group, a halogen atom, an arylazo group, an aryltriazolyl group, an alkylthio group, an arylthio group, an aralkoxycarbonyloxy group, an alkoxycarbonyloxy group, an aryloxycarbonyloxy group, a heterocyclic thio group, a cycloalkylthio group, a cycloalkoxy group, an imido group, an imidazolyl group, a pyrazolyl group, a triazolyl group, an acylamino group, a sulfonamido group or a cycloamino group.

9. A color photographic light-sensitive material as claimed in claim 5, wherein Ar represents an aryl group selected from a phenyl group, a 2-chlorophenyl group, a 4-chlorophenyl group, a 2,5-dichlorophenyl group, a 2,6-dichlorophenyl group, a 2,4,6-trichlorophenyl group, a 2-bromophenyl group, a 3,5-dibromophenyl group, a 2-cyanophenyl group, a 2,6-dichloro-4-cyanophenyl group, a 4-cyanophenyl group, a 4-methylphenyl group, a 2,6-dimethylphenyl group, a 4-butylphenyl group, a 2-trifluoromethylphenyl group, a 2-ethoxyphenyl group, an N-methylbenzamidophenyl group, an N,N-diphenylsulfamoylphenyl group, a phenyl-N-methylsulfonamidophenyl group, a 2,6-dichloro-4-[α-(2,4-di-tert-amylphenoxy)butanamido]phenyl group, a 2,6-dichloro-4-tetradecyloxycarbonylphenyl group, a 2,6-dichloro-4-octadecyloxyphenyl group, a 2,6-dichloro-4-hexadecylthiophenyl group, a 2,6-dichloro-4-octadecylsulfonylphenyl group, a 2,3,4,5,6-pentafluorophenyl group, a 2,3,4,5,6-pentachlorophenyl group, a 2-chloro-5-cyanophenyl group, a 5-chloro-2-methylphenyl group, a 2,6-dichloro-4-methylphenyl group, a 2,4-dichloro-6-methylphenyl group, a 2-chloro-4,6-dimethylphenyl group, a 2,6-dichloro-4-methoxyphenyl group, and a 2,6-dichloro-4-methoxycarbonylphenyl group.

10. A color photographic light-sensitive material as claimed in claim 1, wherein an amount of the coupler is from $2 \times 10^{-3}$ mol to $5 \times 10^{-1}$ mol per mol of silver in the emulsion layer.

11. A color photographic light-sensitive material as claimed in claim 1, wherein the silver halide emulsion layer containing the coupler represented by the general formula (I) is a green-sensitive silver halide emulsion layer.

12. A color photographic light-sensitive material as claimed in claim 11, wherein the color photographic light-sensitive material further includes a red-sensitive silver halide emulsion layer and a blue-sensitive silver halide emulsion layer.

13. A color photographic light-sensitive material as claimed in claim 12, wherein the red-sensitive silver halide emulsion layer contains a phenolic or naphtholic cyan color forming coupler, and the blue-sensitive silver halide emulsion layer contains a benzoylacetanilide or pivaloylacetanilide yellow color forming coupler.

* * * * *